United States Patent [19]
Urry et al.

[11] Patent Number: 5,854,387
[45] Date of Patent: Dec. 29, 1998

[54] SIMPLE METHOD FOR THE PURIFICATION OF A BIOELASTIC POLYMER

[75] Inventors: Dan W. Urry; David T. McPherson; Jie Xu, all of Birmingham, Ala.

[73] Assignees: Bioelastics Research, Ltd.; UAB Research Foundation Ltd., both of Birmingham, Ala.

[21] Appl. No.: 543,020

[22] Filed: Oct. 13, 1995

Related U.S. Application Data

[63] Continuation of Ser. No. 423,516, Apr. 14, 1995, abandoned.

[51] Int. Cl.$^6$ .......................... A61K 38/00; A61K 38/04; C07K 5/00; C07K 7/00
[52] U.S. Cl. .......................... 530/323; 530/330; 530/344
[58] Field of Search .................................... 530/323, 330, 530/344

[56] References Cited

U.S. PATENT DOCUMENTS

| | | | |
|---|---|---|---|
| 4,132,746 | 1/1979 | Urry et al. | 260/857 |
| 4,187,852 | 2/1980 | Urry et al. | 128/334 |
| 4,474,851 | 10/1984 | Urry | 428/373 |
| 4,500,700 | 2/1985 | Urry | 528/328 |
| 4,589,882 | 5/1986 | Urry | 623/11 |
| 4,605,413 | 8/1986 | Urry et al. | 623/11 |
| 4,693,718 | 9/1987 | Urry et al. | 623/11 |
| 4,783,523 | 11/1988 | Urry et al. | 530/323 |
| 4,870,055 | 9/1989 | Urry et al. | 514/12 |
| 4,898,926 | 2/1990 | Urry | 528/328 |
| 4,976,734 | 12/1990 | Urry et al. | 623/11 |
| 5,032,271 | 7/1991 | Urry | 210/350 |
| 5,064,430 | 11/1991 | Urry | 623/1 |
| 5,085,055 | 2/1992 | Urry | 60/527 |
| 5,226,292 | 7/1993 | Urry | 60/721 |
| 5,250,516 | 10/1993 | Urry | 514/17 |
| 5,255,518 | 10/1993 | Urry | 60/527 |

OTHER PUBLICATIONS

Urry et al. (1985) "Carbon–13 NMR Relaxation Studies Demonstrate an Inverse Temperature Transition in the Elastin Polypentapeptide," *Biochemistry* 24:5182–5188.

Urry et al. (1992) "Hydrophobicity Scale for Proteins Based on Inverse Temperature Transitions," *Biopolymers* 32:1243–1250.

McPherson et al. (1992) "Production and Purification of a Recombinant Elastomeric Polypepetide, G–(VPGVG) $_{19}$–VPGV, from *Escherichia coli*.". Biotechnol. Prog. 8:347–352.

Urry, "Angewandte Chemie" (1993) *A Journal of the Gesellschaft Deutscher Chemiker* 32 (6) :767–922.

Urry, et al., "Design at Nanometric Dimensions To Enhance Hydrophobicity–Induced $pK_a$ Shifts" (1992) *J. Am. Chem. Soc.* 114:8716–8717.

Urry, et al., "Delineation of Electrostatic–and Hydrophobic–Induced $pK_a$ Shifts in Polypentapeptides: The Glutamic Acid Residue" (1993) *J. Am. Chem. Soc.* 115:7509–7510.

Rapaka et al., "Coacervation Properties in Sequential Polypeptide Models of Elastin" (1978) *Int. J. Peptide Protein Res.* 12:81–92.

McPherson et al.; Production and Purification of a Recombinant Elastomeric Polypeptide, G–(VPGVG)$_{19}$–VPGV, from *Escherichia coli*; Biotechnol. Prog.; 1992, 8, 347–352.

Urry et al.; Carbon–13 NMR Relaxation Studies Demonstrate an Inverse Temperature Transition in the Elastin Polypentapeptide; Biochemistry; 1985, 24, 5182–5189.

Gruissem & Zurawski, 1985, EMBO J. 4:3375–3383.

Boyer & Mullet, 1986, Plant Molecular Biology 6:229–243.

Scopes, R.K.; Protein Purification (1987) Springer Verlag, New York.

*Primary Examiner*—Cecilia J. Tsang
*Assistant Examiner*—Jennifer Harle
*Attorney, Agent, or Firm*—Cooley Godward LLP

[57] ABSTRACT

A method for purifying an artificial polymer that exhibits a reversible inverse temperature transition is provided. The method involves (a) dissolving the polymer in an aqueous medium so that the temperature of the medium is below the effective transition temperature; (b) adjusting the temperature of the aqueous medium relative to the effective transition temperature of the polymer; (c) removing any particulate material from the medium; (d) adjusting the temperature of the aqueous medium relative to the effective transition temperature of the polymer so that the temperature of the medium is above the effective transition temperature; (e) collecting the polymer from the medium as a more dense phase; and (f) optionally repeating any of steps (a)–(e) until a desired level or purity is reached; with the proviso the order of steps can be (a)-(d)-(e)-(a)-(b)-(c).

19 Claims, 8 Drawing Sheets

FIG. 1A

1.
```
        gly  val  gly  val  pro  (GVGVP)8  gly val gly val pro            CCA GGC GTT GGATCCCG
CGGGATCCA GGC GTT GGT ----------------------------------------------------- GGT CCG CAA CCTAGGGC
GCCCTAGGT CCG CAA CCA                                                           pf1M1   BamH1
   BamH1     pf1M1
```

2.
```
    gly  val  gly  val  pro  (GVGVP)8  gly val gly val pro         CCA GGC G
     TT GGT ------------------------------------------------------- GGT C
     CG CAA CCA
```

3.
```
    (gly val gly val pro (GVGVP)8 gly val gly val pro)n            CCA GGC G
     TT GGT ------------------------------------------------------- GGT C
     CG CAA CCA
```

4.
```
              met      ((GVGVP)10)n   gly  val  gly  val   pro stop
TCGGATCCAGACC ATG GGC G TT -----GGC G    TT GGT GTA CCG TAAGCTTGAATTCGGATCCAG
GACCTCGGTCTGG TAC C    CG CAA-----C    CG CAA CCA CAT GGC ATTCGAACTTAAGCCTAGGTC
   BamH1     Nco1                            Hind3      EcoR1      BamH1
```

FIG.4

```
           P      G     V     G     V     P     G     V
                Pf1M1
cgggat    CCA   GGA   GTT   GGA   GTT   CCT
gcccta    GGT   CCT   CAA   CCT   CAA   GGA
          BamH1

GGT   GTA   GGT   GTA   CCT
                CCA   CAT   CCA   CAT   GGA

GGA   GTT   GGT   GTA   CCT
                CCT   CAA   CCA   CAT   GGA

GGT   GTA   GGA   GTT   CCT
                CCA   CAT   CCT   CAA   GGA

GGA   GTT   GGT   GTT   CCA
                CCT   CAA   CCA   CAA   GGT
                                  Kpn1

GGT   GTA   GGG   GTA   CCT
                CCA   CAT   CCC   CAT   GGA

GGT   GTT   GGT   GTT   CCT
                CCA   CAA   CCA   CAA   GGA

GGA   GTA   GGA   GTA   CCT
                CCT   CAT   CCT   CAT   GGA

GGT   GTT   GGA   GTA   CCC
                CCA   CAA   CCT   CAT   GGG
          Sma1                                Pf1M1
                GGG   GTA   GGT   GTT   CCA   GGA   GTT   GG    atcccg
                CCC   CAT   CCA   CAA   GGT   CCT   CAA   CC    tagggc
                                                                BamH1
``` pHD203-MK-EPSPS-Tp
8145bp

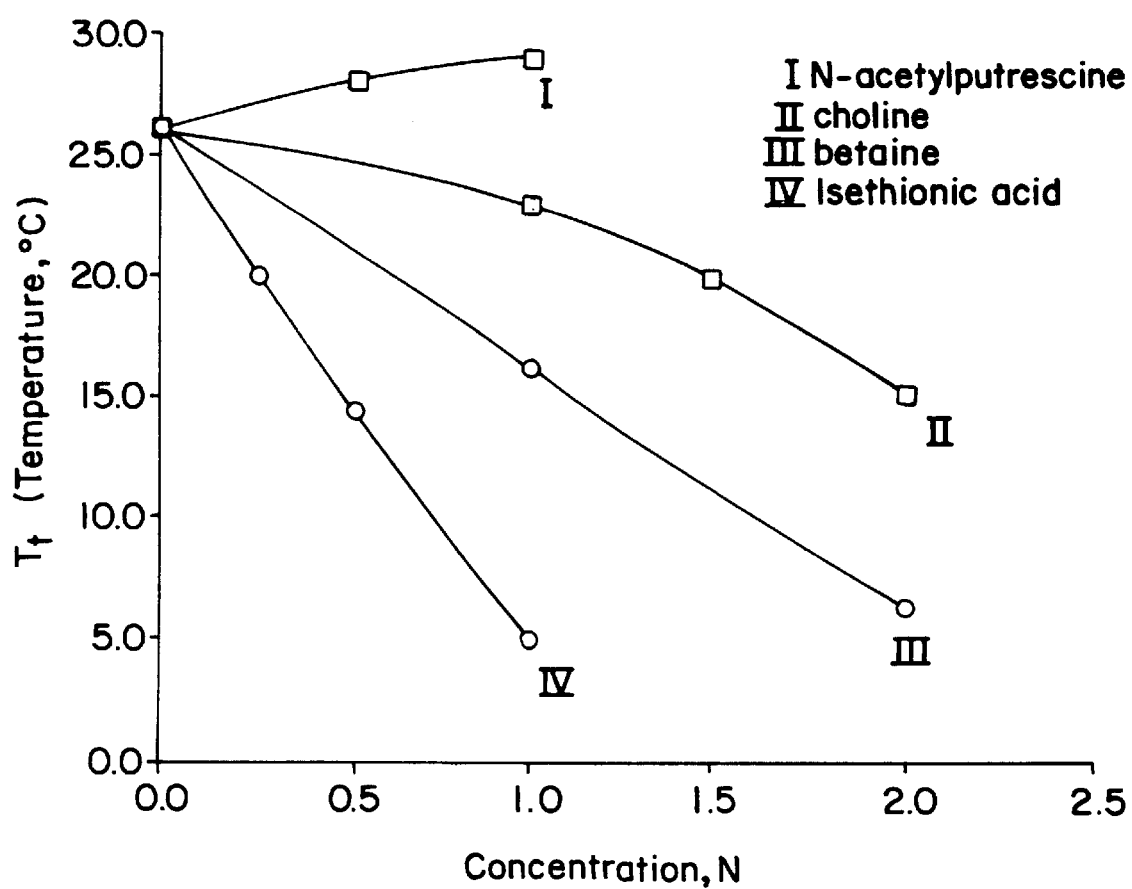

SIMPLE METHOD FOR THE PURIFICATION OF A BIOELASTIC POLYMER

This application is a continuation of Ser. No. 08/423,516, filed Apr. 14, 1995, now abandoned.

TECHNICAL FIELD

The present invention relates generally to the purification of polymers that exhibit inverse temperature transitions.

BACKGROUND

Bioelastomeric polypeptides are a relatively new development that arose in the laboratories of the present inventor and are disclosed in a series of previously filed patents and patent applications. For example, U.S. Pat. No. 4,474,851 describes a number of tetrapeptide and pentapeptide repeating units that can be used to form a bioelastic polymer. Specific bioelastic polymers are also described in U.S. Pat. Nos. 4,132,746, 4,187,852, 4,589,882, and 4,870,055. U.S. Pat. No. 5,064,430 describes polynonapeptide bioelastomers. Bioelastic polymers are also disclosed in related patents directed to polymers containing peptide repeating units that are prepared for other purposes but which can also contain bioelastic segments in the final polymer: U.S. Pat. Nos. 4,605,413, 4,976,734, and 4,693,718, entitled "Stimulation of Chemotaxis by Chemotactic Peptides"; 4,898,926, entitled "Bioelastomer Containing Tetra/Pentapeptide Units"; 4,783,523 entitled "Temperature Correlated Force and Structure Development of Elastin Polytetrapeptide"; 5,032,271, 5,085,055 and 5,255,518, entitled "Reversible Mechanochemical Engines Comprised of Bioelastomers Capable of Modulable Temperature Transitions for the Interconversion of Chemical and Mechanical Work"; 4,500,700, entitled "Elastomeric Composite Material Comprising a Polypeptide"; and 5,520,516 entitled "Bioelastomeric Materials Suitable for the Protection of Wound Repair Sites." A number of other bioelastic materials and methods for their use are described in pending U.S. patent applications including: U.S. Ser. No. 184,873, filed Apr. 22, 1988, entitled "Elastomeric Polypeptides as Vascular Prosthetic Materials"; and U.S. Ser. No. 07/962,608, filed Oct. 16, 1992, entitled "Bioelastomeric Drug Delivery System," U.S. Ser. No. 08/187,441, filed Jan. 24, 1994, entitled "Photoresponsive Polymers"; and U.S. Ser. No. 08/246,874, filed May 20, 1994, entitled "Elastomeric Polytetrapeptide Matrices Suitable for Preventing Adhesion of Biological Materials." All of these patents and patent applications are herein incorporated by reference, as they describe in detail bioelastomers and/or components thereof that can be purified by the methods of the present invention.

Bioelastic materials have been proposed for a number of uses and apparatuses, as indicated by the general subject matter of the applications and patents set forth above. The bioelastic compositions and machines respond to pressure, chemical, and/or thermal changes in the environment by phase transitions (e.g. viscosity or turbidity changes) or by contraction or relaxation to transduce these energies reversibly into mechanical work (for example, as described in U.S. Pat. No. 5,226,292).

The bioelastomeric polymers have considerable potential for use in medical and other applications. However, at present the commercial use of these bioelastomers is limited by the difficulty in large-scale preparation of purified bioelastomers. Typically, the bioelastomeric units of the polymer have been chemically synthesized by processes which are expensive and time-consuming. Expression of the polypeptides using genetic engineering techniques have been successful. However, especially for in vivo use, the polypeptides must be purified with a minimum of contamination from the proteins co-expressed by the host organism. Conventional protein purification schemes generally result in lengthy and expensive procedures that may produce purified product, but with unsatisfactory yields (McPherson et al., (1992) Biotechnol. Prog. 8:347–352).

SUMMARY OF THE INVENTION

Accordingly, it is an object of the present invention to provide a simple process for purifying polymers that exhibit inverse temperature transition to a high degree of purity for their commercial application. It is a further object of the invention to provide a method for purifying bioelastomers irrespective of their source. The method is particularly advantageous for purifying a bioelastomeric polypeptides from complex mixtures of proteins, such as those found after expression of the bioelastomeric polypeptides in a host. In addition, the method can be used to purify chemically synthesized peptides. During peptide synthesis, some amino acids are coupled to the growing peptide chain more easily than others. In synthesizing a bioelastomer or during polymerizations bioelastomers of different lengths are produced having different $T_t$s. This is more apparent with peptide chains of shorter length. The method can therefore be used to allow purification of a range of lengths or maximum chain length depending on their $T_t$s. According to the present invention, the process comprises adjusting the relative temperature of an aqueous medium containing the polymer with respect to the effective transition temperature of the polymer so that the temperature of the aqueous medium is at or below the effective transition temperature, removing material of greater density from the medium, adjusting the relative temperature of the aqueous medium to the effective transition temperature of the polymer so that the temperature of the aqueous medium is at or above the effective transition temperature/functional hydrophobicity of the polymer and collecting material of the more dense phase comprising the polymer from the medium. These steps can be repeated until the desired level of purity is reached. The adjustment of conditions during the purification process can be achieved by numerous methods which include adjusting the temperature, pH or salt concentration of the aqueous media; or adjusting the transition temperature of the polymer by redox, barochemical or photochemical means.

BRIEF DESCRIPTION OF THE DRAWINGS

The invention will be better understood by reference to the following detailed description of specific embodiments with the figures that form part of this specification, wherein.

A. 1. The synthetic gene for $(GVGVP)_{10}$ (SEQ ID NOS: 2 and 3) with flanking external BamH1 and internal PflM1 restriction endonuclease recognition sites. The gene and plasmid pUC118 were each cleaved with BamH1 and mixed together with ligase, to recircularize the plasmid with the gene inserted. The plasmid with the cloned gene was amplified in E. coli. 2. A large-scale plasmid preparation was cleaved with PflM1 and the released $(GVGVP)_{10}$ fragment was purified. 3. The purified PflM1 fragment was self-ligated to form the concatemer genes. 4. Addition of adaptor oligonucleotides to the ligation reaction provides terminal sequences containing restriction sites needed for cloning the $(GVGVP)_n$ genes into various expression plasmids.

Although the genes are referred to in multiples of 10, the adaptor oligonucleotides provide an additional pentamer sequence resulting in $[(10)_n]+1$.

B. Schematic illustration of events described in A.

Figure 2:
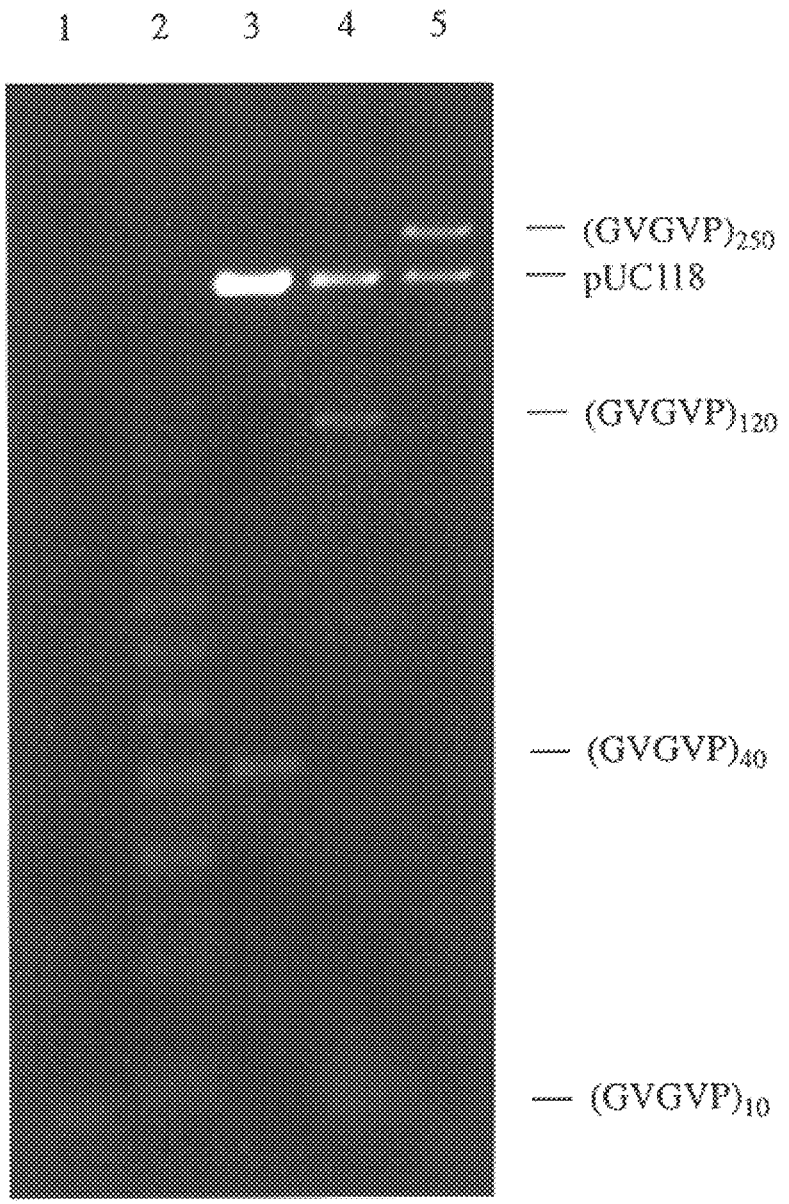

FIG. 2 is a schematic diagram of DNA samples electrophoresed through an agarose slab gel, stained with ethidium bromide and visualized with UV light. Lane 1: The $(GVGVP)_{10}$ PFlM1 gene fragment. Lane 2: The concatemer "ladder" formed by ligation/polymerization of the gene in the presence of adaptor oligonucleotides. Lane 3: The $(GVGVP)_{40}$ gene released from the plasmid pUC118 by the restriction endonuclease BamH1. Lane 4: The $(GVGVP)_{120}$ gene released from the pUC118 by BamH1. Lane 5: The $(GVGVP)_{250}$ gene released from pUC118 by BamH1.

Figure 3:
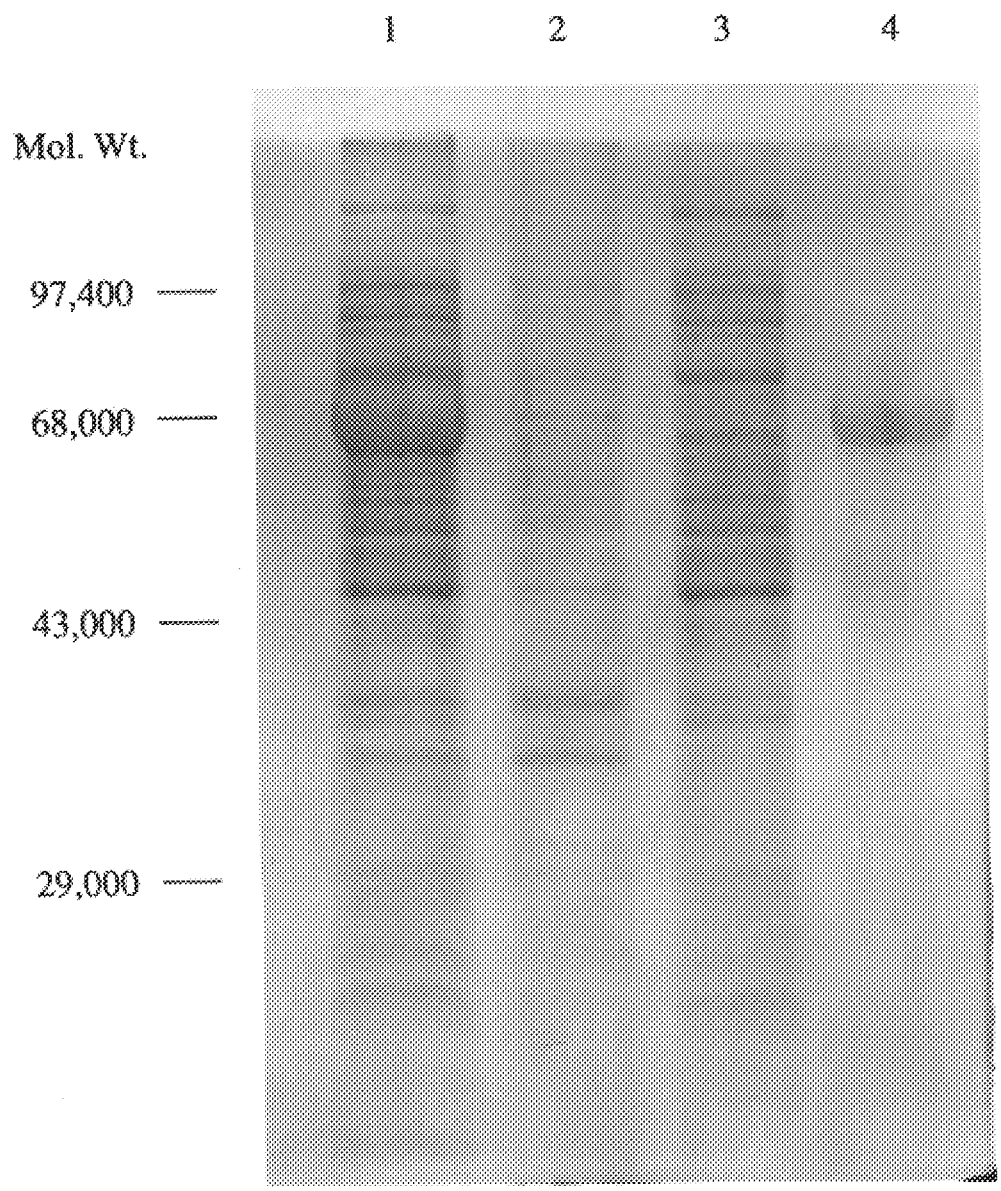

FIG. 3 is a schematic diagram of an analysis of microbially expressed $(GVGVP)_{140}$ (SEQ ID NO:1) by sodium dodecyl sulfate polyacrylamide gel electrophoresis after staining with copper chloride. Lane 1: Crude *E. coli* cell lysate containing $(GVGVP)_{140}$ (SEQ ID NO:1). Lane 2: Insoluble cell debris and non-lysed cells removed by centrifugation of cold (4° C.) lysate. Lane 3: Cell lysate after removal of $(GVGVP)_{140}$ (SEQ ID NO:1). Lane 4: The protein-based polymer removed from the cell lysate by centrifugation following thermally induced aggregation.

FIG. 4 depicts the sequence of the $(GVGVP)_{10}$ gene for tobacco (SEQ ID NO:6).

Figure 5:
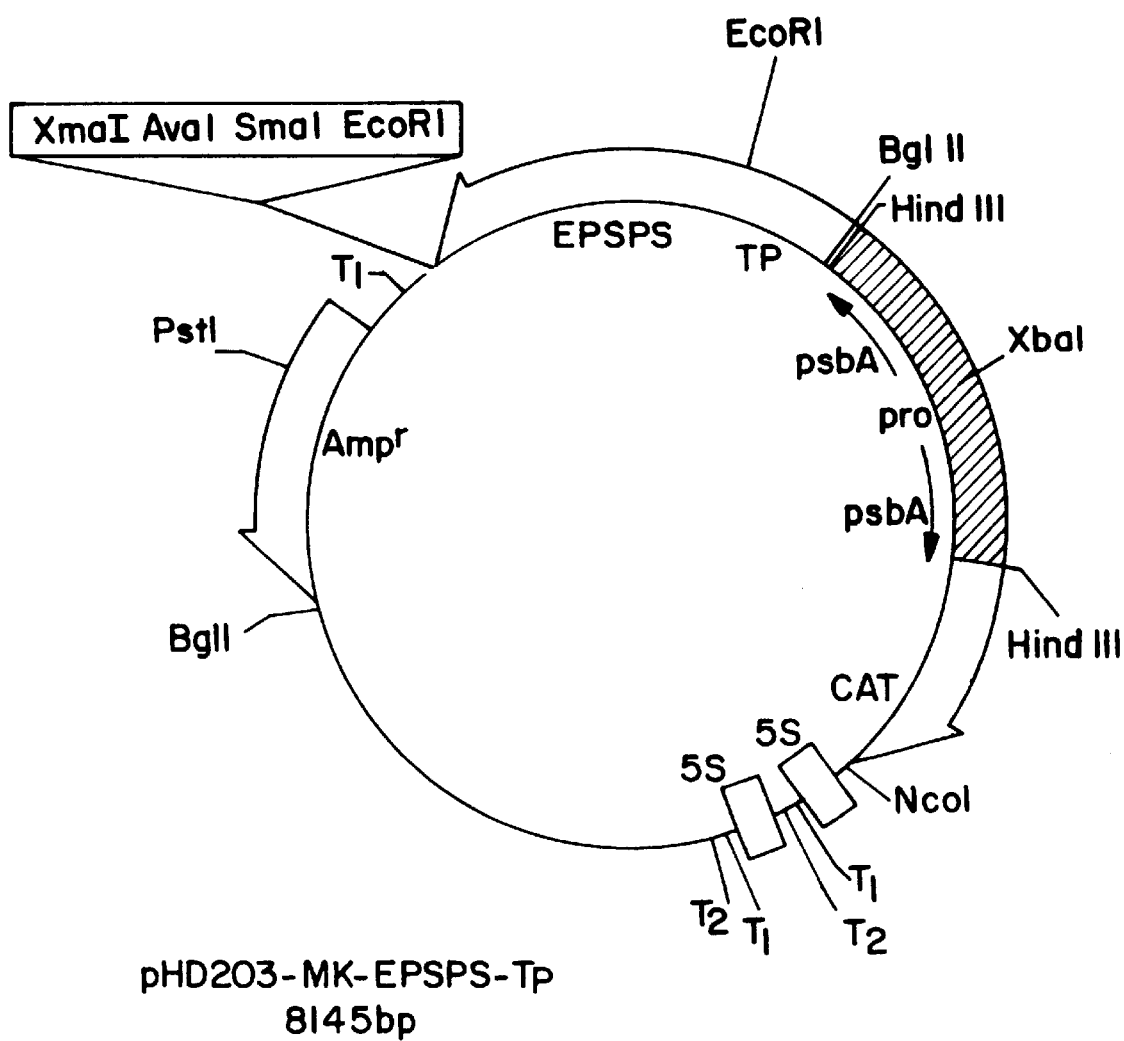

FIG. 5 is a schematic diagram of the plasmid pHD203-GUS-EPSPS (EN/polyA).

FIG. 6 is a schematic diagram showing the effect of natural solutes associated with adhesive glycoproteins of the spider orb web on the effective transition temperature.

Figure 7A:
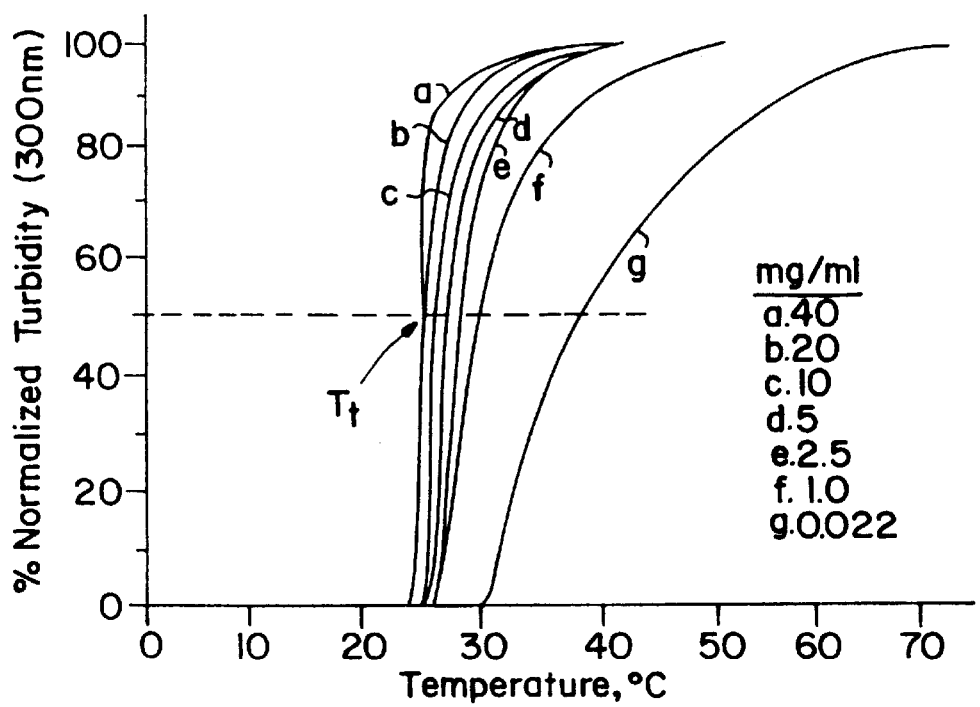
Figure 7B:
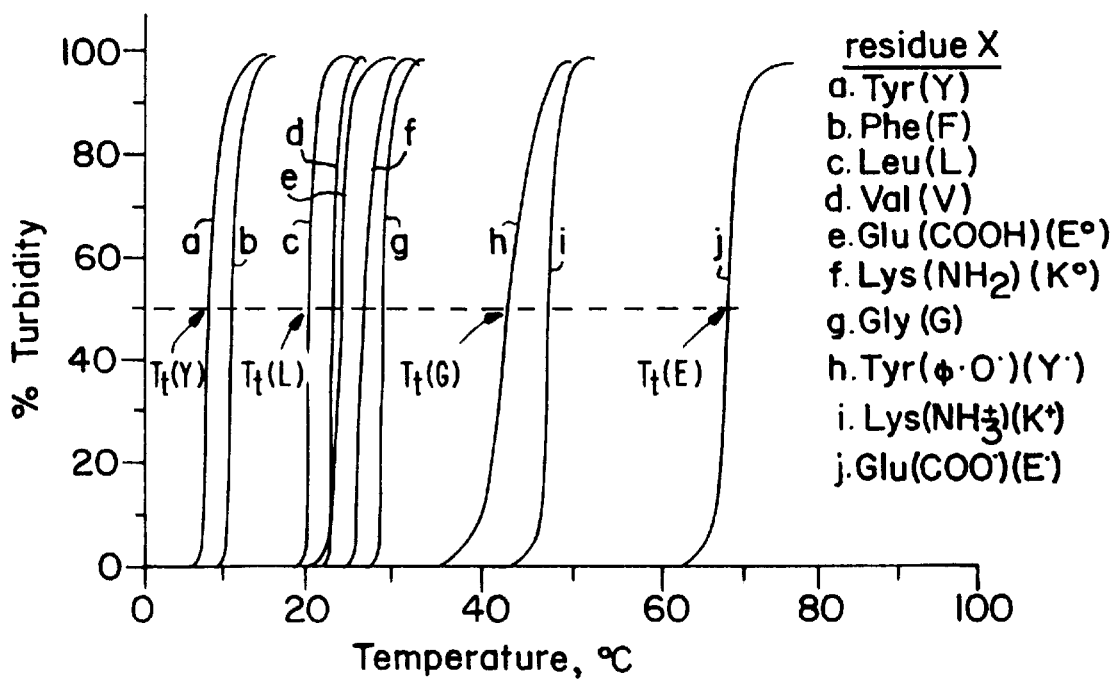

FIG. 7 is a schematic diagram showing a series of temperature profiles for turbidity depending on polymer concentration.

DESCRIPTION OF SPECIFIC EMBODIMENTS

The method of the present invention can be used to purify polymers that exhibit an inverse temperature transition. The term inverse temperature transition refers to the phase transition of certain polymers to a condensed state of greater order in water on raising the temperature through the transition temperature range, and the temperature at which the onset of this transition occurs is designated as the transition temperature ($T_t$) (Urry (1992); Urry (1993a) Angew. Chem., 105:859–883; Urry, D. W. (1993b) Angew. Chem. Int. Ed. Engl., 32:819–841). Typically, these polymers contain both polar and hydrophobic regions.

In its broadest aspect, the method of the present invention comprises: (a) dissolving a polymer exhibiting inverse temperature transition in an aqueous medium, (b) adjusting the relative temperature of the aqueous medium to the effective transition temperature of the polymer so that the temperature of the aqueous medium is below the effective transition temperature, (c) removing material of greater density from the medium, (d) adjusting the relative temperature of the aqueous medium to the effective transition temperature of the polymer so that the temperature of the aqueous medium is above the effective transition temperature of the polymer, (e) collecting material of the more dense phase comprising the polymer from the medium, and (f) optionally repeating any of steps (a)–(e) until a desired level of purity is reached; with the proviso the order of steps can be (a)-(d)-(e)-(a)-(b)-(c) at any point in the method.

Although the invention can be carried out with a number of different polymers, this specification exemplifies the invention by concentrating on bioelastic polypeptides, a class of polymers originally identified by the inventor. The bioelastic polymers are described in detail in the various patents and other documents listed above. Bioelastic polymers comprise repeating units that form β-turns. A β-turn is a 10-atom hydrogen-bonded ring in which the C=O of amino acid residue i is hydrogen-bonded to the NH of residue i+3. Repetitive β-turns result in elastic β-spiral structures.

A fundamental property common to bioelastic polymers is that they are soluble in water at a sufficiently low temperature, but that they hydrophobically fold and associate to form a separate phase as the temperature is raised through a particular temperature range (Urry, D. W. (1992) Prog. Biophys. Molec. Biol., 57:23–57). The temperature for this phase transition, commonly called coacervation, is determined by the hydrophobicity of the amino acids comprising the polymer. When more hydrophobic amino acids are included, the temperature is decreased, and when less hydrophobic amino acids are included, the temperature is increased. The dependence of the temperature range for the phase transition on the hydrophobicity of the composite amino acids provides the basis for a hydrophobicity scale dependent on the hydrophobic folding process of interest (Urry, D. W. (1993a and 1993b); Urry, et al. (1992) Biopolymers, 32:1243–1250). The hydrophobicity scale based thereon is called the $T_t$-based hydrophobicity scale for protein and protein-based polymer engineering. The phase transition can occur reversibly or irreversibly upon raising the temperature. For example, plastic β-spiral structures form irreversibly for poly(APGVGV) (SEQ ID NO:7), and reversibly for poly(VPAVG) (SEQ ID NO:8). The latter can exhibit elasticity below and through much of the transition temperature range but becomes a hard plastic once the transition is complete. Because of this, the material may be referred to as an inverse thermoplastic.

Table 1 provides a hydrophobicity scale for poly[fv(VPGVP)fx(VPGXG)] (SEQ ID NOS:1 and 9) as an example, where fv and fx are mole fractions with fv and fx=1, where X is any of the naturally occurring amino acid residues or chemical modifications thereof, and $T_t$ is defined as the temperature of half maximal turbidity. It should be noted that the location of the "X" residue in the polymer is not critical and was made in these examples principally for ease of synthesis. Some variations in properties do occur with substitution of other amino acid residues in the pentameric elastomer unit. The specific location of any modification of the polymer is not important as long as the bulk properties of the polymer are maintained.

The $T_t$-based hydrophobicity scale depicted in Table 1 is useful for protein engineering of bioelastic polymers. When a functional side chain or sequence is introduced, for example, to achieve a given free energy transduction, then residue X may be varied to place the value of $T_t$ as desired for the intended protein function. When a given hydrophobic side chain in the repeating pentamer of a protein polymer is replaced by one having an additional hydrophobic $CH_2$ moiety, the value of $T_t$ is lowered in direct proportion to the number of added $CH_2$ moieties. When a given hydrophobic side chain in the protein polymer is replaced by one having fewer $CH_2$ moieties, as when Val is replaced by Ala, the value of $T_t$ is raised in direct proportion to the number of $CH_2$ moieties removed. Thus the value of $T_t$ is clearly related to the hydrophobicity with lower values of $T_t$ indicating greater hydrophobicity and higher values of $T_t$ indicative of more polar or less hydrophobic residues. The temperature at which the folding and assembly occur can, therefore, be shifted and thus folding and assembly can occur without a change in temperature. This is referred to as the $\Delta T_t$ mechanism.

The temperature at which folding and assembly occur can be changed by altering a number of intrinsic or extrinsic factors. Intrinsic to a class of model proteins of 50,000 Da molecular weight or greater are: (a) the concentration of polymer itself, (b) changes in the amino acid composition within the polymeric bioelastic unit, (c) changes in the degree of ionization of functional side chains controlled by changes in pH, (d) the phosphorylation of side chains such as serine by enzymes called kinases, (e) the oxidation or reduction electrically, chemically or enzymatically of a side chain attached to the polymer, (f) photochemical reactions of attached chromophores and (g) chemical reactions of side chains in response to electromagnetic radiation.

Extrinsic chemical changes affecting $T_t$ include the effects of salts, organic solutes and pressure. U.S. Pat. No. 5,226, 292 from the laboratory of the present inventors details pressure-related effects. In addition there is a chain length dependence that becomes significant at lower molecular weights where shorter chain lengths result in higher values of $T_t$.

TABLE 1

Temperature of the inverse temperature transition, $T_1$ for poly[fv(VPGVP)fx(VPGXG) (SEQ ID. NOS: 1 and 9)].
$T_1$ values are linearly extrapolated to fx = 1.

| Amino acid residue X | $T_1$ [°C.] | Correlation coefficient |
|---|---|---|
| Lys(NMeN, red.)[a] | −130 | 1.000 |
| Trp (W) | −90 | 0.993 |
| Tyr (Y) | −55 | 0.999 |
| Phe (F) | −30 | 0.999 |
| His (pH 8) (H) | −10 | 1.000 |
| Pro (P) | (−8) | [b] |
| Leu (L) | 5 | 0.999 |
| Ile (I) | 10 | 0.999 |
| Met (M) | 20 | 0.996 |
| Val (V) | 24 | [c] |
| Glu(COOCH$_3$)(E$^m$) | 25 | 1.000 |
| Glu(COOH)(E) | 30 | 1.000 |
| Cys (C) | 30 | 1.000 |
| His (pH 4) (H$^+$) | 30 | 1.000 |
| Lys(NH$_2$) (K) | 35 | 0.936 |
| Asp(COOH) (D) | 45 | 0.994 |
| Ala (A) | 45 | 0.997 |
| HyP | 50 | 0.998 |
| Asn (N) | 50 | 0.997 |
| Ser (S) | 50 | 0.997 |
| Thr (T) | 50 | 0.999 |
| Gly (G) | 55 | 0.999 |
| Arg (R) | 60 | 1.000 |
| Gln (Q) | 60 | 0.999 |
| Lys(NH$_3^+$)(K$^+$) | 120 | 0.999 |
| Tyr(⊖-O)(Y) | 120 | 0.996 |
| Lys(NMeN, ox.) [a] | 120 | 1.000 |
| Asp(COO)(D) | 170 | 0.999 |
| Glu(COO)(E) | 250 | 1.000 |
| Ser(PO) | 1000 | 1.000 |

[a] NMeN represents N-methylnicotinamide pendant on a lysyl side chain, i.e., N-methylnicotinate attached by amide linkage to the ε-NH$_2$ of lysine. The reduced state is N-methyl-1,6-dihydronicotinamide residue. [b] Calculated. [c] Serves as reference substance.

When the temperature is raised through the range of the inverse temperature transition, the cross-linked matrix contracts. Alternatively, instead of changing the temperature, it is possible to change the value of $T_t$ as described above. This means, for example, if $T_t$ is just above the operating temperature and an energy input is introduced which lowers the value of $T_t$ to below the operating temperature, that the energy input will also drive contraction. If the energy input is a change in the concentration of a chemical, i.e., chemical energy, then chemo-mechanical transduction will have occurred. By means of suitably reactive or responsive groups being a part of the protein-based polymer, it is also possible using the elastic matrices to demonstrate baro-mechanical, electromechanical, and photo-mechanical transductions. While these energy conversions are achieved by changing the value of $T_t$ and while they utilize hydrophobic folding or unfolding, they do not involve the performance of mechanical work which is so readily a part of folding and unfolding. These are called second-order molecular machines of the $T_t$-type, and they include the ten pairwise energy conversions involving the energy inputs of temperature changes, pressure changes, chemical concentration changes, electrochemical oxidations or reductions, and the absorption or dissipation of electromagnetic radiation (Urry, 1993a and 1993b; Urry, 1992). Similarly, the properties of uncross-linked polymers can be altered to change the value of $T_t$ in order to induce coacervation. This ability to change the properties of the bioelastic polymers by altering the value of $T_t$ is exploited in the present invention to allow purification of the polymers. The relative temperature of the polymer to the effective $T_t$ can be adjusted by altering the ambient temperature or, as described above, influencing the effective $T_t$ by varying the energy input e.g., pressure changes, chemical concentration changes, electrochemical oxidations or reductions, etc.

Using the relative hydrophobicities of the amino acid side chains, it is possible to construct polymers which will exhibit inverse temperature transitions by a systematic, knowledge-based approach. This approach can be used with natural compounds where there is stereochemical regularity, as well as with entirely synthetic molecules.

The structure of bioelastomers are described in detail in various patents and patent applications that arose from the laboratories of the present inventor. Considerable variations in the amino acids that are present at various locations in the resulting polymer is possible as long as the multiple β-turns with intervening suspended bridging segments are retained in order to preserve elasticity. It is possible to prepare polypeptides in which monomeric units are interspersed throughout a larger polypeptide that contains peptide segments designed for other purposes. The location of a random or systematic substituent in the polymer, with respect to the monomer residue side-chain position, is not critical so long as the beta-turn is not prevented from forming in the relaxed state. Preferred positions for the various peptides of the invention are as taught in the patents and pending applications from the laboratory of the present inventor in this area, which have been incorporated by reference. For example, the bioelastomer can contain naturally occurring sequences which are components of connective tissue. These can be insertions of, for example, single amino acids between monomeric units, substitutions of one amino acid for another in an occasional monomer, or inclusion of different polypentapeptide, polyhexapeptide or polytetrapeptide sequences which can be added either in parallel or in sequence to increase strength, elastic modulus and ease of handling, as disclosed, for example, in U.S. Pat. Nos. 4,474,851 and 5,064,430. The bioelastic units of the invention can be attached to or interspersed among other types of molecules, which molecular units can impart functions to the polymer such as biological activity, chemotaxis, drug attachment, protease, or nuclease susceptibility. These molecular units can be added covalently and sequentially or as side chains to provide for the desired properties. The ratio of these other molecular units to the monomer residue can range from 1:2 to 1:5000. Preferably the ratio is 1:10 to 1:100. The upper limit on the number and kind of substituents is also influenced by the ability of the elastic polymer to fold/assemble properly to attain a beta-spiral in the relaxed state. Such molecules include peptides, proteins, nucleic acid, DNA, RNA, carbohydrates and lipid chains. The preferred polymers to be purified by the methods of the present invention are protein and protein-based bioelastomers. Most preferred are those containing bioelastic pentapeptides, tetrapeptides, and nonapeptides.

In general, selection of the sequence of amino acids in a particular monomeric unit and selection of the required proportion of monomeric units can be accomplished by an empirical process that begins with determining (or looking up) the properties of known bioelastomers, making similar but different bioelastomers using the guidance provided in this specification, and measuring the transition temperature as described herein and in the cited patents and patent applications. Preferably, however, one uses tables of relative hydrophobicity of amino acid residues (either naturally occurring or modified) to compute the transition temperature without experimentation. For example, see Y. Nozaki and C. Tanford, (1971) *J. Biol. Chem.* 246:2211–2217, or H. B. Bull and K. Breese, (1974) *Archives Biochem. Biophys.* 161:665–670, for particularly useful compilations of hydrophobicity data. For example, a rough estimate can be obtained of the likely transition temperature by summing the mean hydrophobicities of the individual amino acid residues, or their side chain modified forms, in the monomeric units of the polymer and comparing the result to the sum obtained for polymers having known transition temperatures.

More accurate values can be calculated for any given polymer by measuring transition temperatures for a series of related polymers in which only one component is varied. For example, polymers that mostly contain VPGVG (SEQ ID NO:1) with varying amounts of VPGXG (SEQ ID NO:9) monomers (e.g., 2%, 4%, and 8% X) can be prepared and tested for transition temperatures. The test merely consists of preparing the polymer in uncrosslinked form, dissolving the polymer in water, and raising the temperature of the solution until turbidity appears, which indicates the precipitation of polymer from solution. If the transition temperatures are plotted versus the fraction of VPGXG (SEQ ID NO:9) monomer in the polymer, a straight line is obtained, and the fraction of VPGXG (SEQ ID NO:9) necessary for any other desired temperature (within the limits indicated by 0% to 100% of the VPGXG (SEQ ID NO:9) monomer) can be obtained directly from the graph. When this technique is combined with the rough estimating ability of hydrophobicity summing as described above, any desired transition temperature in the range of liquid water can be obtained.

In terms of a generalized hydrophobicity scale, the COOH moiety is more hydrophobic than the COO⁻ moiety. The transition temperature can be lowered simply by decreasing the pH and raised by increasing the pH of the medium contacting a bioelastic polymer when a carboxylate group is present (or other group capable of forming an ion upon increasing the pH). If an intermediate temperature is maintained, then a 20 Mrad crosslinked matrix of poly[4 (VPGVG),1(VPGEG)] (SEQ ID NOS:1 and 10), that is, a random copolymer in which the two pentameric monomers are present in a 4:1 ratio, where E=Glu, will precipitate on lowering the pH and dissolve on raising the pH. The temperature of the transition in phosphate buffered saline will shift some 50° C. from about 20° C. at low pH, giving COOH, to nearly 70° C. at neutral pH where all the carboxyls have been converted to carboxylate anions. By choosing a side chain group whose protonation/deprotonation can be modulated one can in turn modulate the response of the polymer to changes in pH.

Usually, the sequences of the bioelastic monomer units are chosen for their specific properties which provide for their utility (e.g., in prosthetic devices, drug delivery, etc.) as described in the various patents and patent applications of the present inventor. However, knowing the sequences and ratios of the monomeric units within the polymer allows one to determine, or at least estimate, the effective $T_t$ of the polymer as described above. This will be dependent on the hydrophobicity of the polymer. It may be emphasized here that any chemical means of changing the mean hydrophobicity of the polymer, such as an acid-base titratible function, dephosphorylation/phosphorylation, reduction/oxidation of a redox couple, etc., can be used to bring about coacervation/dissolution at an estimatable $T_t$.

For example, sodium chloride lowers the value of $T_t$ 14° C. $N^{-1}$ (i.e., gram equivalent per liter for poly (VPGVG) (SEQ ID NO:1) whereas NaBr is less effective in lowering $T_t$. The most potent salts on a normality basis are those with multivalent anions such as carbonates, sulfates and phosphates. It should be noted that NaI and NaSCN cause small increases in the value of $T_t$.

Organic solutes appear to be more variable than the salts and a few are even biphasic in their effects. Organic solutes in order of decreasing potency that raise $T_t$ are sodium dodecylsulfate (600° C. mol$^{-1}$ at 0.1M), guanidine hydrochloride (12° C. mol$^{-1}$ at 0.3M), urea (5.5° C. mol$^{-1}$ at 0.3M) and Triton X-100 which is biphasic (22° C. mol$^{-1}$ at 0.3M). Organic solutes that lower $T_t$ are ethylene glycol, trifluoroethanol (−11° C. mol$^{-1}$ at 0.4M), trifluoracetic acid and glycerol (−2.2° C. mol$^{-1}$ at 0.4M). Dimethyl sulfoxide and also ethylene glycol (at very low concentrations) are biphasic, increasing the value of $T_t$ at lower concentrations. Of particular interest are a set of natural solutes that are associated with adhesive glycoproteins of the spider orb web. These are N-acetylputrescine, choline, betaine and isethionic acid, and their effects on $T_t$ are given in FIG. 6. Interestingly, most of these lower the temperature for phase separation.

Increases in pressure will raise the value of $T_t$ and will do so most effectively if there are aromatic residues present such as Phe(F), Tyr() and Trp(W). Although not wishing to be bound by any theory, the effect is thought to occur because the volume occupied per water molecule is less than when the water molecules are more-ordered surrounding aromatic moieties than when they are less-ordered bulk water. This means that application of pressure could be used to drive solubilization and the release of pressure could bring about phase separation. These effects with aromatic residues are relevant to the pressures developed during centrifugation and, therefore, should be considered when using centrifugation as a purification step.

When the concentration of a bioelastic polymer is increased, the temperature of the inverse temperature transition decreases to a high concentration limit which occurs at about 40 mg/mL. In FIG. 7 are given a series of temperature profiles for turbidity formation (Tpτ curves) wherein the temperature for the onset of turbidity decreases and the steepness of the curve increases as the concentration is increased to a high concentration limit of 40 mg/mL. The temperature, $T_t$, of the inverse temperature transition is defined as the temperature at which 50% of the normalized turbidity is obtained. Accordingly, the concentration of polymers of different compositions should be kept in mind when examining other means of changing the value of $T_t$.

An effective means of raising the value of $T_t$ is to increase the degree of ionization, α, of an amino acid residue such as Asp (COO⁻), Lys (NH$_3^+$) or Glu (COO⁻) present in a polymer as described above. With known compositions and pKa values, changes in pH become a very effective means of achieving solubilization or separation of the polymer. Similarly, chemical reduction using, for example, dithionite reduces the value of $T_t$.

The bioelastic matrices, whether formed from elastic β-spiral structures or from reversible plastic β-spiral structures, result from cross-linking of the individual polymer chains. Cross-linking of a polymer solution to form an elastic matrix can be performed using various cross-linking process, e.g. chemical, photochemical, enzymatic, irradiative after introduction of suitably reactive moieties. U.S. Pat. No. 4,589,882, incorporated herein by reference, teaches enzymatic cross-linking by synthesizing block polymers having enzymatically cross-linkable units.

In order to obtain high molecular weight polymers in good yields, a number of approaches are available. When producing polymers by chemical synthesis, care should be taken to avoid impurities, because small levels of impurities can result in termination of the polymerization process or in racemerization that can alter the physical properties, in particular the inverse temperature transition, of the resulting polymer, but there are otherwise no particular problems of synthesis. Different bioelastomer unit permutations have been prepared and polymerized with different coupling methods, and are described in detail in the patents and patent applications listed above. Peptide unit purity is important in obtaining a material with suitable physical properties, since small changes in the preparation of the monomers can result in a transition temperature that varies as much as 15° C. (25° C.–40° C.). This variance is important to consider since a polymer that has a 25° C. transition temperature will form a very good cross-linked elastomeric matrix, while a preparation having a 40° C. transition temperature will not cross-link to form an elastomeric matrix. Moreover, accuracy in the estimation of the transition temperature for a polymer is of advantage in the methods of the present invention to keep unnecessary preliminary testing to a minimum and for reproducibility. The solution of this potential problem is simply to purify the components used to prepare the peptide. Synthesis of the bioelastomeric repeating units is straightforward and easily accomplished by a peptide chemist.

An alternative to the organic synthesis of protein-based polymers is a biosynthetic approach using current recombinant DNA methodologies. Using this approach, a gene encoding the desired peptide sequence is constructed, artificially inserted into, and then translated in a host organism. The host can be eukaryotic, e.g. yeast, plant or prokaryotic, e.g. bacteria. Usually, the host will be microbial, where the resulting protein can then be purified, often in large amounts, from cultures grown in fermentation reactors. Recombinant DNA can be used to create synthetic genes encoding multiple repeating units of a given peptide sequence and these synthetic genes may themselves be polymerized to create even longer coding sequences, resulting in protein-based polymers of greater length.

A wide variety of genes or gene fragments are useful in forming fusion sequences with bioelastic sequences. Any selected, desired DNA sequence can be used as long as the bulk properties of the bioelastomers are not impaired. Desired peptides or proteins can include any peptide or protein useful for human or veterinary therapy, diagnostic or research applications in any expression system. For example, hormones, cytokines, growth or inhibitory factors, enzymes, modified or wholly synthetic proteins or peptides can be produced according to this invention in bacterial, yeast, plant, mammalian or other eukaryotic cells and expression systems suitable therefor. For example, these may include IL-1, MIP-1α, IL-6, M-CSF, IL-2, IL-3, IL-4, IL-5, LIF, MIF (macrophage inhibitory factor), or a variety of small peptides of random sequence. The ratio of these other molecular units to the monomer residue is as described above with the proviso that the elastic polymer still has the ability to attain a beta-spiral in the relaxed state.

Techniques known in the art are used to manipulate the genetic information (i.e., DNA sequences) for their effective expression in the appropriate host organism (see, for example, Sambrook et al., (1989) Molecular Cloning: A Laboratory Manual, Second Edition, Cold Spring Harbor, N.Y.; Deguchi et al., (1993) Mat. Res. Soc. Symp. Proc., 292:205–210; Capello, J. (1992) in Review Protein Engineering Biomaterial, Curr. Opin. Struct. Biol., 2:582–586; McPherson et al. (1992); Perbal, B. (1988) In A Practical Guide to Molecular Cloning, 2nd Ed., John Wiley & Sons NY; Ausubel, F. M. (1989) In Current Protocols in Molecular Biology, Vols 1 & 2, John Wiley & Sons NY). The primary tools that make this possible are known in the art and include enzymes capable of cleaving, joining, copying and otherwise modifying polynucleotides. In addition, vectors allowing the introduction of this information into the host organism in a suitable manner for expression are also known in the art.

For example, DNA fragments having restriction sites at their proximal ends and encoding bioelastomeric polypeptides can be synthesized, using oligonucleotides designed to have appropriate nucleotides at their 5' proximal ends that form restriction sites when double-stranded, and have complementarity at their 3' ends sufficient to promote annealing and extension using a polymerase (usually by PCR). This approach can be employed to provide DNA fragments that can be incorporated into expression vectors at appropriate restriction sites for their expression in a host in large quantities. Alternatively, shorter oligonucleotides encoding bioelastomer monomer units can be ligated to each other for expression. Using this approach, several levels of complexity are possible. 1.) A single pair of oligonucleotides can be annealed and ligated to give a concatemer with each tandem repeat of the monomer having an identical sequence. 2.) Two or more pairs of oligonucleotides can be used, each with a different composition of allowable codons but maintaining pair-to-pair overlap complementarity. These can be annealed separately and ligated together, or both annealed and ligated as a single mix. This results in the formation of a concatemer gene with a corresponding level of codon diversity. 3.) A single pair of "degenerate" oligonucleotides can be synthesized each with the appropriate mix of bases at the codons' third positions to reflect host codon preference.

Adaptor oligonucleotides are added to the ligation reactions to select and clone concatemers. Generally the concatemers will be of a size that can be easily sequenced using flanking primers (e.g., 300–400 bp). The adaptor oligonucleotides can also be used to create terminal restriction enzyme recognition sites that allow excision of the gene for further multimerization to the desired size range (e.g., 150 catemers). Additional adaptor oligonucleotides can be included in this ligation reaction to allow cloning of the multimer gene into the proper vector for expression in the host system.

A detailed example of the production of poly-VPGVG is set out in McPherson et al., "Production and Purification of a Recombinant Elastomeric Polypeptide, G-(VPGVG)$_{19}$-VPGV (SEQ ID NO:1), from *Escherichia coli*," Biotechnol. Prog., 1992:347–352, a publication arising from the laboratory of the present inventor. This publication can be used as guidance for genetic-based production of the material of the present invention. However, this method relies on an expensive inducer, IPTG, for gene expression, and an expensive protease, factor Xa, for cleavage of the polypentapeptide away from the glutathione S-transferase carrier protein. A more cost effective manner for expressing the bioelastmer would be advantageous. For example, bioelastomeric polymers having no methionines in their sequence can be expressed as recombinant fusion proteins designed to incorporate a methionine residue at the fusion junction. Preferably, there would be no methionines in the bioelastomeric polypeptide, allowing cleavage of the fusion protein using cyanogen bromide (G. Allen, (1989) "Sequencing of Proteins and Peptides," in Laboratory Techniques in Biochemistry and Molecular Biology; R. H. Bundon et al. Eds, Elsevier, N.Y.,) to release the leader peptide. Alternatively, less expensive enzymatic means of cleavage, such as cleavage following a lysine or arginine by trypsin, can be employed to remove the leader peptide where lysine or arginine is not present within the bioelastomer or protein of interest.

Other expression systems can also be employed, such as, expression utilizing the bacteriophage lambda temperature-inducible promoter system, a promoter/expression system that is widely used for large-scale production of recombinant proteins in *E. coli*. Several expression plasmids based on this system are available commercially (e.g. Pharmacia). Promoter function is regulated by a temperature sensitive repressor protein. At the permissive growth temperature of 30° C. promoter function is repressed; upon shifting the temperature to 37°–42° C. the promoter is de-repressed and the gene is expressed. This temperature shift can be easily and economically achieved in standard large-scale fermentors.

Crop production of the bioelastomers is also an economically viable alternative. *E. coli* and chloroplasts have interchangeable transcriptional/translational machinery (Gruissem and Zurawski, (1985) EMBO J. 4:3375–3383; Boyer and Mullet, (1986) Plant Molecular Biology 6:229–243) and bacterial genes driven by bacterial promoters have been expressed in chloroplasts (Daniell and McFadden, (1987) Proc Natl. Acad. Sci. USA 84:6349–6353). Vectors for transfecting plant cells are known in the art and may optionally allow for parallel expression of a marker gene, such as chloramphenicol acetyl transferase (cat) or β-glucuronidase (uid A), or contain a strong promoter or an enhancer, etc. (Daniell and McFadden, (1991) Plant Cell Reports 9:615–619; Daniell, H., et al., (1990) Proc. Natl. Acad. Sci. USA 87:88–92; Ye, G. N., et al., (1990) Plant Mol. Biol. 15:809–820; Daniell, H., (1993) Methods Enzymol. 217:536–556). The nucleic acid constructs are then used to transfect a host organism. Methods for transforming plants are known in the art (Shimamoto, K., et al. (1989) Nature 338:274–277; Datta, S. K., et al. (1990) Bio/Technology 8:736–740; Cristov, P., et al. (1991) Bio/Technology 9:957–962; Gordon-Kamm, W. J., et al. (1990) The Plant Cell 2:603–618; Fromm, M. E., et al. (1990) Bio/Technology 8:833–839; Vasil, V., et al. (1992) Bio/Technology 10:667–674; Weeks, J. T., et al. (1993) Plant Physiol. 102:1077–1084; Somers, D. A., et al. (1992) Bio/Technology 10:1589–1594; Bower, R. and Birch, R. G. (1992) Plant J. 2:409–416; Kung, S. and Wu, R. (1993) Transgenic Plants Engineering and Utilization 1:382; Daniell, H. (1993) Methods in Enzymol. 217:536–556).

One potential problem associated with the expression of protein-based polymers may be the presence of methionine encoded by the start codon of the polymer gene, which may modify reactivity of an elastomeric polypeptide although, in terms of hydrophobicity, it is very similar to the valyl residue. This problem can be overcome by chemical cleavage of the peptide after isolation or by targeting the polypeptide using a suitable transit peptide sequence. Several transit peptide sequences have been successfully used to target foreign proteins (Cheng et al. (1988) Proc. Natl. Acad. Sci. USA 85:391–395). The transit peptide is cleaved as the protein is transported into, for example, the chloroplast or intercellular spaces, simplifying purification. One of the unique advantages in expressing polymers within organelles is that chloroplasts can be isolated by homogenization of the tissue in an isotonic buffer and pelleted by low speed centrifugation. Chloroplasts can then be lysed in a hypotonic buffer to release the elastic and plastic protein-based polymers. In addition, exposure of polymers to alkaloid is minimized by expressing them inside chloroplasts. Proteins can also be extracted from intercellular spaces by a simple vacuum infiltration-centrifugation procedure. This procedure washes out contents of the intercellular space and reduces exposure of polymers to alkaloids.

There appears to be no upper limit to the molecular weight of useful polymers that can be purified by the methods of the invention except that imposed by the processes of making these polymers. Polymers containing up to about 250 pentamers have been synthesized in *E. coli* using recombinant DNA methods. Typical polymers contain at least 5, preferably at least 10, more preferably at least 20, tetrapeptide or pentapeptide monomers, and because of poor solubility in aqueous solvents, which are desirable for biological uses as well as the method of the present invention, usually contain fewer than 1000, usually fewer than 500, of such units.

After synthesis, the polymer is usually dissolved in an aqueous medium as a first step in the purification. The media employed may include small amounts of polar organic solvents, usually less than 40 volume percent, more usually less than about 10 volume percent. The solutions can be buffered at a pH in the range from about 6 to 9, more usually from about 7 to 8.5. Various buffers may be employed, such as phosphate, Tris, or the like. When the polymer is synthesized by a host, lysing the cells to provide the polymer in an aqueous medium is herein considered equivalent to dissolving the polymer in an aqueous medium. Methods for providing expressed proteins in solution are known in the art. For example, methods for providing bacterial lysates and plant extracts are described by Scopes, R. K. (1987) in Protein Purification, Springer Verlag, N.Y.

The relative temperature of the medium with respect to the effective transition temperature is then adjusted either to be above or below the effective transition temperature. The effective transition temperature has been defined as the temperature at which 50% maximum turbidity is obtained for a polymer in solution. Generally, the relative temperature of the medium is adjusted so that at least 50% of the polymer is in one phase, preferably at least 75%, most preferably at least 95%.

In the case that the temperature of the medium is below the effective transition temperature, the dense phase, whether particulate or viscoelastic, is removed leaving the polymer of interest in solution. Techniques for providing the temperature of the medium below the $T_t$ are described above and include decreasing the temperature, increasing the pH of the medium, decreasing the salt concentration of the medium (e.g., by dialysis), increasing pressure (e.g., by increasing centrifugal force), increasing light irradiation (if certain photoactivatable groups are present in the polymer), or by oxidation, etc. Similarly, conditions providing the temperature of the medium above the effective $T_t$ include increasing the temperature, decreasing the pH, increasing the salt concentration of the medium, etc. In this case, the polymer of interest is recovered in the dense phase.

The dense phase can be removed by any available means, e.g., filtration, or centrifugation. If the polymer is initially recovered by collecting the dense phase (whether particulate or viscoelastic), it is necessary to dissolve the material in an aqueous medium for further purification. The adjustment of the relative temperature of the aqueous medium can be carried out as described above in order to dissolve the polymer. The contaminating particulate material is then removed leaving the polymer in solution, which can be further purified or concentrated if required, for example, by again adjusting the relative temperature of the sample allowing the polymer to coacervate.

Conventional purification techniques (Scopes, 1987) such as ion exchange chromatography, affinity chromatography, gel filtration, preparative gel electrophoresis etc. can be used in conjunction with the method of the present invention.

The invention now being generally described, the same will be better understood by reference to the following examples, which are provided for purposes of illustration only and are not to be considered limiting of the invention.

EXAMPLES

Example 1

Expression of Gene Constructs Encoding a Bioelastic Polymer in E. coli

Figure 1B:
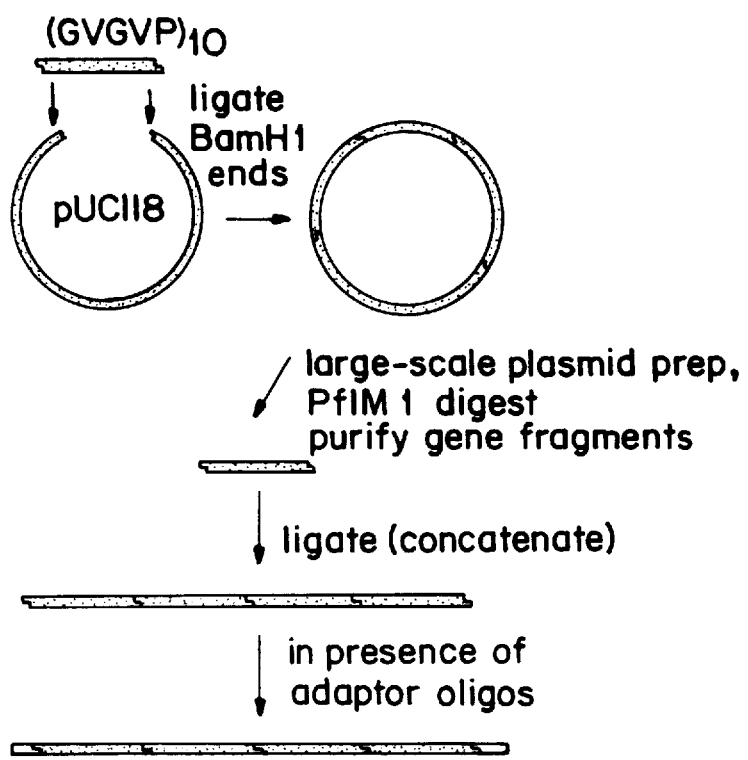
FIG. 1 is a schematic illustration of the cloning steps of $(GVGVP)_n$ (SEQ ID NO:1) genes.

The $(GVGVP)_{120}$ (SEQ ID NO:1) was constructed using synthetic oligonucleotides having the sequence depicted in FIG. 1 (SEQ ID NOS:2 and 3). The oligonucleotides were flanked with sequences containing the BamH 1 (G'GATCC) and PflM 1 (CCAGGCGTTGG) (SEQ ID NO:11) restriction endonuclease recognition sites. This nucleic acid was inserted into the plasmid pUC118 and used to transform E. coli. After isolating the amplified plasmid, the sequence of the gene insert was verified by DNA sequence analysis (Sambrook et al., Molecular Cloning: A Laboratory Manual, Second Edition, Cold Spring Harbor, N.Y. (1989)).

This 10mer gene was then used as a modular unit for constructing longer genes encoding $(GVGVP)_n$ (SEQ ID NO:1) of higher molecular weights. Plasmid containing the 10mer gene was prepared and digested with PflM 1. The PflM 1 $(GVGVP)_{10}$ gene fragments were then purified and used in subsequent ligation reactions to form polymers of $[(GVGVP)_{10}]_n$ (SEQ ID NO:1). Also, separate adaptor oligonucleotides with unique restriction sites were added to this ligation reaction to allow the subsequent cloning of the concatenated gene fragments. These adaptor oligonucleotides were added at a ratio that would favor the recovery of high molecular weight "concatemers". This process is represented schematically in FIG. 1B.

For recovery and cloning of individual length concatemer genes, the ligation mixture was digested with BamH1 then electrophoresed through an agarose slab gel to achieve separation of the various molecular weight sizes. Slices corresponding to different size ranges then were removed from the gel, the DNA was recovered, and then cloned into plasmid pUC118 (Urry et al. "Elastic and Protein-based Polymers: Potential for Industrial Uses, (Am. Chem. Soc.) Div. Polym. Mat.: Sci & Engr., "Industrial Biotechnological Polymers," Washington D.C., 1994). Gene inserts into this plasmid were analyzed by restriction endonuclease digestion and accurately sized by agarose gel electrophoresis adjacent to a concatemer "ladder" (See FIG. 2). To achieve expression of a native protein-based polymer in E. coli, a concatemer gene encoding $(GVGVP)_{120}$ (SEQ ID NO:1) was subcloned from pUC118 into the expression vector pQE-32 (Quiagen, Inc.) as a gene fusion behind a sequence encoding six tandem histidines. Expression using this plasmid resulted in the production of proteins with an amino-terminal polyhistidine fusion, specifically, $MRGSH_6GIQTM-(GVGVP)_n$ (SEQ ID NO:12). This fusion moiety provides the ability to affinity purify the protein by metal-chelate chromatography. Several different sized concatemer genes were subcloned into and expressed from the pQE-32 vector in E. coli. The poly(GVGVP) polymers (SEQ ID NO:1) that were produced were affinity purified from the bacterial cells and shown to have the requisite glycine, valine and proline at the expected ratios for poly(GVGVP) (SEQ ID NO:1) by amino acid analysis of phenylisothiocyanate (PITC) derivatives of the amino acids separated by reverse phase liquid chromatography. This established that genes encoding protein-based polymers of high molecular weight, for example, $(GVGVP)_{250}$ (SEQ ID NO:1), can be made and efficiently expressed in an E. coli host organism; using a gene fusion and affinity purification approach it was also possible to highly purify the recombinant protein and show that it was the desired product.

Purification of Expressed Product

Using affinity purified $MRGSH_6GIQTM-(GVGVP)_{120}$ (SEQ ID NO:12), it was shown that the protein-based polymer reversibly precipitates (i.e., coacervates) by raising and lowering the temperature; this coming out and into solution could be determined visually by watching the liquid go cloudy and then clear.

This property was used to purify histidine fusion proteins comprising $(GVGVP)_n$ (SEQ ID NO:1) where n=40, 140 and 250. First, a chilled (on ice) suspension of E. coli cells containing the protein-based polymer was lysed by sonic disruption to disperse the cellular components. At cooler temperatures, the poly(GVGVP) (SEQ ID NO:1) remains in the unfolded soluble state and the insoluble cell debris can be removed by centrifugation. While still cold, the lysate was centrifuged at high speed to remove the insoluble cell debris. The recovered supernatant was then warmed to 37° C. causing the protein-based polymers to form a visible aggregate, at which point it was removed from the soluble fraction by centrifugation. Upon heating to above its transition temperatures of 37° C., the poly(GVGVP) species (SEQ ID NO:1) forms a new phase which allows for selective removal by centrifugation from the remaining solute. Repeating this procedure once again, as a wash, resulted in product that was as pure as the affinity purified material when analyzed by SDS-polyacrylamide gel electrophoresis (See FIG. 3). In this way, over 90% bacterial endotoxin was removed.

Example 2

Expression and Purification of Native Poly $(GVGVP)_{120}$ in E. coli

To achieve expression of a native protein-based polymer in E. coli, a concatemer gene encoding $(GVGVP)_{120}$ (SEQ ID NO:1) was subcloned from pUC118 described in Example 1 into the expression vector pET-11d (Novagen, Inc.) as a Nco1 to BamH 1 fragment. The protein was expressed at high levels from this plasmid without the amino-terminal affinity moiety previously described. It was also effectively purified as described in Example 1 using the temperature induced aggregation procedure.

Example 3

Expression of Elastic Protein-Based Polymer, Poly (GVGVP) in Tobacco Chloroplasts Genes encoding the poly(GVGVP) protein (SEQ ID NO:1) in the range of 150 tandem pentapeptide units are constructed for expression in tobacco systems using synthetic oligonucleotides and PCR, to encode 10 repeating units of the GVGVP (SEQ ID NO:1). FIG. 4 shows the sequence of the gene (SEQ ID NO:6), comprising optimal codons for tobacco while maintaining maximal coding degeneracy. The gene is constructed using two oligonucleotides, each representing just over half of the gene. The oligonucleotides have complementary 25 base overlaps (dotted underline in figure) at their 3' ends that are extended by the PCR reactions to form the full-length double-stranded sequence. The PCR product is digested with BamH1 and inserted into plasmid pUC119 for sequence confirmation and continued maintenance. The fragment is excised from pUC119 using PflM 1 and self-ligated to form concatemers, with the inclusion of adaptor fragments to terminate multimerization in the desired size range.

The synthetic gene is introduced into chloroplasts of cultured tobacco cells using the Gene Gun, essentially as described by Daniell (Methods Enzymol. 217 (1993) 536–556). After continued growth of transformed cells in MS salt medium in the presence of $^{35}S$ methionine, chloroplasts are isolated using a Mini-bead beater (Daniell et al. (1993) Nucleic Acids Res. 21:1503–1504). Soluble chloroplast proteins are obtained by rupturing chloroplasts in hypotonic buffer. The bioelastomer is purified essentially as described in Example 1.

Example 4

Expression of Plastic Protein-Based Polymer, Poly (AVGVP) (SEQ ID NO:8), from Tobacco For construction of the gene encoding poly(AVGVP) (SEQ ID NO:8) in the range of 150 repeating units for expression in tobacco, a different concatemeric approach is used. Specifically, two 15 base degenerate oligonucleotides, 5' CCNGCNGTNGGNGTN 3' (SEQ ID NO:13) and 5' CNGGNACNCCNACNG 3' (SEQ ID NO:14), are synthesized (where N=G,A,T or C), each representing one strand of a double-stranded unit encoding the (AVGVP) monomer (SEQ ID NO:8), with codon choice for tobacco. The two strands are offset such that they anneal leaving 4–5 base overlapping ends that are complementary, allowing joining of the 5' ends to the 3' ends. The annealed oligonucleotides, or catemers, are ligated through their complementary ends to form long multimers, or concatemers, as described above for the $(GVGVP)_{10}$ genes. Expression and purification of the bioelastomeric polypeptides are essentially as described above, with the exception that the transition temperature for poly (AVGVP) (SEQ ID NO:8) is used.

Example 5

Expression of poly(VPGVG) (SEQ ID NO:1) After Stable Chloroplast or Nuclear Transformation The plasmid pHD203-GUS-EPSPS (EN/polyA) (see FIG. 4) contains CaMV 35S promoter/enhancer elements driving the aroA gene (coding for EPSP synthase conferring resistance to glyphosate) and flanked at the 3' end by a polyA fragment to stabilize the transcript. The coding sequence for G-$(VPGVG)_{19}$-VPGV (SEQ ID NO:1) (the 20mer) fused with the gst coding sequence is inserted at the BglII site in pHD203-GUS-EPSPS-(EN/polyA) using adaptors or by filling in the recessed 3' end termini using Klenow fragment of E. coli DNA polymerase I. Stable expression is achieved by bombarding the EPSPS vector containing gst-EG20mer coding sequences into cultured tobacco cells and growing them in the presence of glyphosate. The coding sequences are inserted into the region between rbcL and ORF 52 of the tobacco chloroplast genome in order to accomplish a high frequency of transformation (Svab and Maliga, (1993) Proc. Natl. Acad. Sci. USA 90 913–917).

Transgenic tobacco plants expressing polymers inside chloroplasts are obtained by bombarding leaves from aseptically grown plants with chloroplast vectors. Calli formed on selection media are regenerated. Optimal conditions for selection and regeneration of tobacco chloroplast transgenic plants is known in the art (Svab et al., (1990) Proc. Natl. Acad. Sci USA 87:8526–8530; Staub and Maliga, (1992) The Plant Cell 4:39–45; Svab and Maliga (1993) Proc. Natl. Acad. Sci. USA 90:913–917.

Molecular and Biochemical Analyses of Chloroplast Transformants

Chloroplast DNA is isolated from transgenic plants by methods known in the art. Ethidium bromide stained gels of restriction digested ctDNA preparations are examined to detect additional ctDNA fragments; insertion of the EPSPS/gst-EG20mer fragment from chloroplast vectors into tobacco ct genomes introduce additional restriction sites into ct genomes of transgenic plants. ctDNA is digested with restriction enzyme and separated by electrophoresis on agarose gels and blotted onto nylon membranes. Fragments containing EPSPS or gst or polymer coding sequences are used as hybridization probes. All transgenic lines are tested for the presence of EPSPS-gst-polymer coding sequences in tobacco chloroplast genomes. Chloroplast extracts are prepared and protein purified as described in Example 3.

Example 6

Stable Nuclear Expression of Protein-Based Polymers in Transgenic Tobacco

The synthetic gst-G-$(VPGVG)_{19}$-VPGV gene cassette (SEQ ID NO:1) (Mc Pherson et al.) is inserted into a pKYLX vector (Schardl et al., (1987) Gene 61:1–11) as follows. The MaeI/EcoR1 fragment containing the cassette is modified to incorporate a new ATG codon through addition to a Xho/Nco1 adapter (5'-TCGAGCCATGG-3'/3'-CGGTACC-5') (SEQ ID NO:15) to the 5' end and moved into pKLYX7.1 as a Xho1/EcoR1 fragment. pKLYX7.2, a derivative of pKYLX7.1 (Daniell et al. (1986) Proc Natl. Acad Sci. USA 83:248–255) wherein the Xba1 site has been replaced with an EcoR1 site is employed to receive the gst-G-$(VPGVG)_{19}$-VPGV cassette.

Young, fully expanded tobacco leaves (Nicotiana tabacum cv KY 14) are taken from 8-week-old plants and surface sterilized for 10 min with 10% chlorox, followed by 3 min in 70% alcohol and washed 3 times with sterile distilled water. Agrobactenum tumefaciens-mediated leaf disk transformation and shoot regenerations are performed as described by Horsch et al. (1985) Science 227:1229–1231). Briefly, putative transformants are selected on MS media containing 300 mg/L kanamycin and 500 mg/L mefoxin as described by Svab et al. (Proc. Natl. Acad. Sci.

USA (1990) 87:8526–8530). Kanamycin resistant shoots are transferred to rooting media. Approximately 50 kanamycin-resistant plantlets are selected for analysis. Control plants are transformed with pKYLX7.2 alone.

Putative transformants are verified by Southern hybridization and assayed for NPTII phosphotransferase activity as well as for production of the gst-G-(VPGVG)$_{19}$-VPGV (SEQ ID NO:1) protein (McPherson et al.). Selected individual transformants are selected to produce a homozygotic individual that is used as an initial progenitor for seeds to be used in field studies. Approximately 1 acre is planted with each type of transgenic tobacco. Smaller plots of vector-only transformed plants and nontransformed plants serve as controls for growth comparison or other assessments. Seedlings are greenhouse propagated and transplants are planted in research plots. Cell extracts are prepared (Scopes et al.) and polymers purified as described in Example 1.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method for purifying a bioelastic polymer comprising pentapeptide or tetrapeptide repeating units, wherein said repeating units exist in a conformation having a β-turn and said polymer exhibits a reversible inverse temperature transition, comprising:

(a) dissolving said polymer in an aqueous medium, (b) adjusting the temperature of said aqueous medium to the effective transition temperature of said polymer so that the temperature of said aqueous medium is below said effective transition temperature, (c) removing any particulate material from said medium, (d) adjusting the temperature of said aqueous medium to the effective transition temperature of said polymer so that the temperature of said aqueous medium is above the effective transition temperature of said polymer, (e) collecting dense phase material comprising said polymer from said medium, and (f) optionally repeating any of steps (a)–(e) until a desired level of purity is reached;

with the proviso the order of steps can be (a)-(d)-(e)-(a)-(b)-(c) during said method.

2. The method of claim 1, wherein said adjusting comprises a change in temperature of said aqueous media.

3. The method of claim 1, wherein said adjusting comprises a change in salt concentration of said aqueous media.

4. The method of claim 1, wherein said adjusting comprises a change in applied pressure to said polymer.

5. The method of claim 4, wherein said change in applied pressure results from centrifugal force.

6. The method of claim 1, wherein said adjusting comprises a change in the redox state of said polymer.

7. The method of claim 1, wherein said adjusting comprises a change in chemical potential of said polymer.

8. The method of claim 1, wherein said adjusting comprises irradiating said polymer.

9. The method of claim 1, wherein said polymer is recovered in said collected particulate material.

10. The method of claim 1, wherein said polymer is recovered in solution.

11. The method of claim 1, wherein said polymer comprises a bioelastomer.

12. The method of claim 11, wherein said polymer further comprises a non-elastomeric polypeptide.

13. The method of claim 11, wherein said bioelastomer is elastin.

14. The method of claim 1, wherein said polymer is a recombinant protein.

15. The method of claim 1, wherein said aqueous medium is a bacterial lysate.

16. The method of claim 1, wherein said aqueous medium is a plant extract.

17. The method of claim 1, wherein said polymer comprises a chemically synthesized polymer.

18. The method of claim 1, wherein said particulate material is removed by centrifugation.

19. The method of claim 1, wherein said particulate material is removed by filtration.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:1:

Gly  Val  Gly  Val  Pro
     1                       5

( 2 ) INFORMATION FOR SEQ ID NO:2:

( i ) SEQUENCE CHARACTERISTICS:
        ( A ) LENGTH: 18 base pairs
        ( B ) TYPE: nucleic acid
        ( C ) STRANDEDNESS: double
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:2:

CGGGATCCAG GCGTTGGT                            18

( 2 ) INFORMATION FOR SEQ ID NO:3:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:3:

CCAGGCGTTG GATCCCG                             17

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:4:

```
TCGGATCCAG ACCATGGGCG TT                                              22
```

( 2 ) INFORMATION FOR SEQ ID NO:5:

( i ) SEQUENCE CHARACTERISTICS:
        ( A ) LENGTH: 36 base pairs
        ( B ) TYPE: nucleic acid
        ( C ) STRANDEDNESS: double
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:5:

```
GGCGTTGGTG TACCGTAAGC TTGAATTCGG ATCCAG                               36
```

( 2 ) INFORMATION FOR SEQ ID NO:6:

( i ) SEQUENCE CHARACTERISTICS:
        ( A ) LENGTH: 173 base pairs
        ( B ) TYPE: nucleic acid
        ( C ) STRANDEDNESS: single
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:6:

```
CGGGATCCAG GAGTTGGAGT TCCTGGTGTA GGTGTACCTG GAGTTGGTGT ACCTGGTGTA     60
GGAGTTCCTG GAGTTGGTGT TCCAGGTGTA GGGGTACCTG GTGTTGGTGT TCCTGGAGT     120
GGAGTACCTG GTGTTGGAGT ACCCGGGGTA GGTGTTCCAG GAGTTGGATC CCG           173
```

( 2 ) INFORMATION FOR SEQ ID NO:7:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:7:

```
Ala  Pro  Gly  Val  Gly  Val
 1                 5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:8:

Val  Pro  Ala  Val  Gly
    1                           5

( 2 ) INFORMATION FOR SEQ ID NO:9:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:9:

Val  Pro  Gly  Xaa  Gly
    1                           5

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:10:

Val  Pro  Gly  Glu  Gly
    1                           5

( 2 ) INFORMATION FOR SEQ ID NO:11:

( i ) SEQUENCE CHARACTERISTICS:
        ( A ) LENGTH: 11 base pairs
        ( B ) TYPE: nucleic acid
        ( C ) STRANDEDNESS: double
        ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:11:

CCAGGCGTTG G                                                         11

( 2 ) INFORMATION FOR SEQ ID NO:12:

( i ) SEQUENCE CHARACTERISTICS:
   ( A ) LENGTH: 20 amino acids
   ( B ) TYPE: amino acid
   ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO:12:

Met Arg Gly Ser His His His His His His Gly Ile Gln Tyr Met Gly
 1               5                      1 0                     1 5

Val Gly Val Pro
              2 0

( 2 ) INFORMATION FOR SEQ ID NO:13:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:13:

CCNGCNGTNG GNGTN                                                           1 5

( 2 ) INFORMATION FOR SEQ ID NO:14:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:14:

CNGGNACNCC NACNG                                                           1 5

( 2 ) INFORMATION FOR SEQ ID NO:15:

( i ) SEQUENCE CHARACTERISTICS:
      ( A ) LENGTH: 11 base pairs
      ( B ) TYPE: nucleic acid
      ( C ) STRANDEDNESS: single
      ( D ) TOPOLOGY: linear ( i i ) MOLECULE TYPE: DNA (synthetic)

( i i i ) HYPOTHETICAL: NO ( i v ) ANTI-SENSE: NO ( x i ) SEQUENCE DESCRIPTION: SEQ ID NO:15:

TCGAGCCATG G                                                               1 1